United States Patent

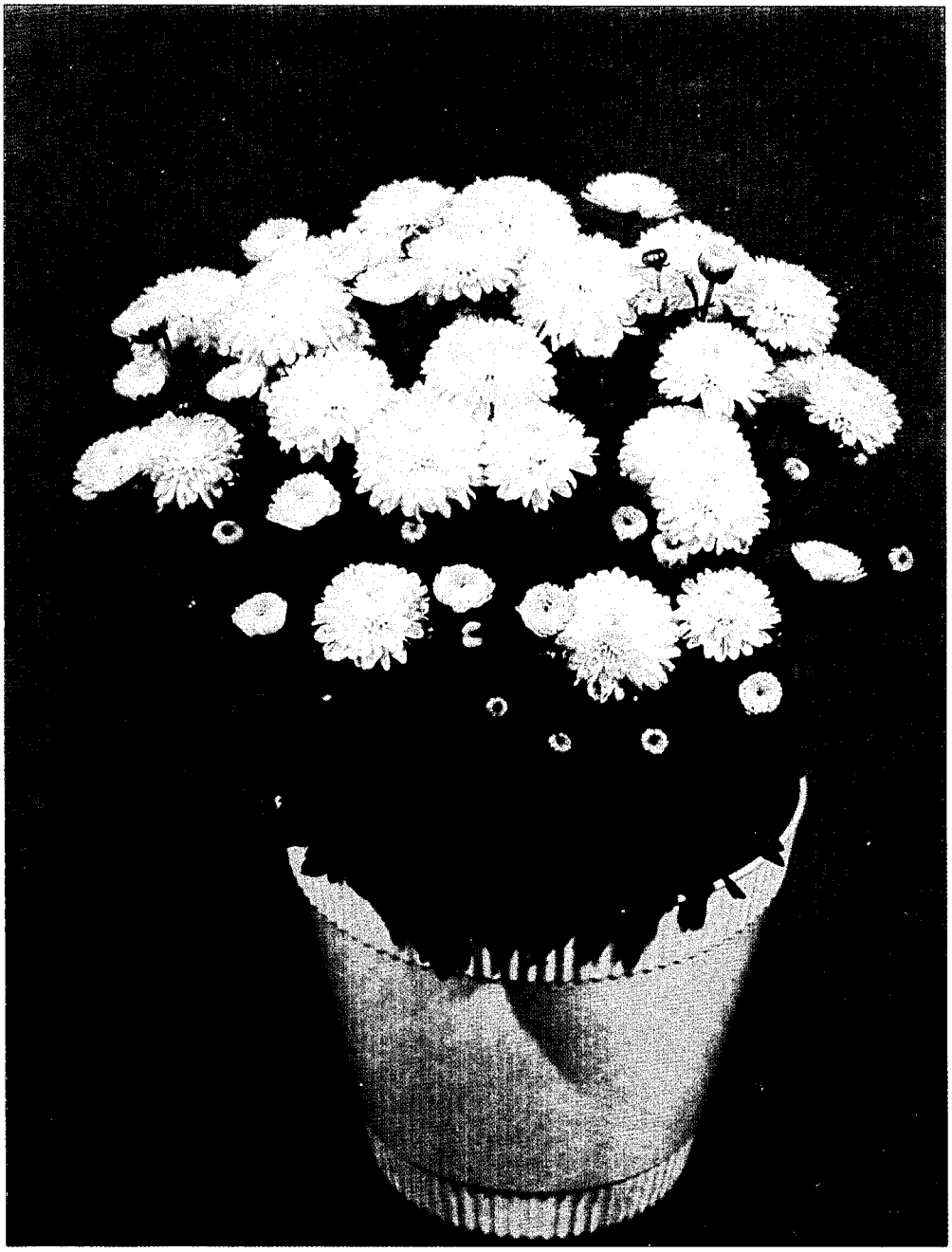

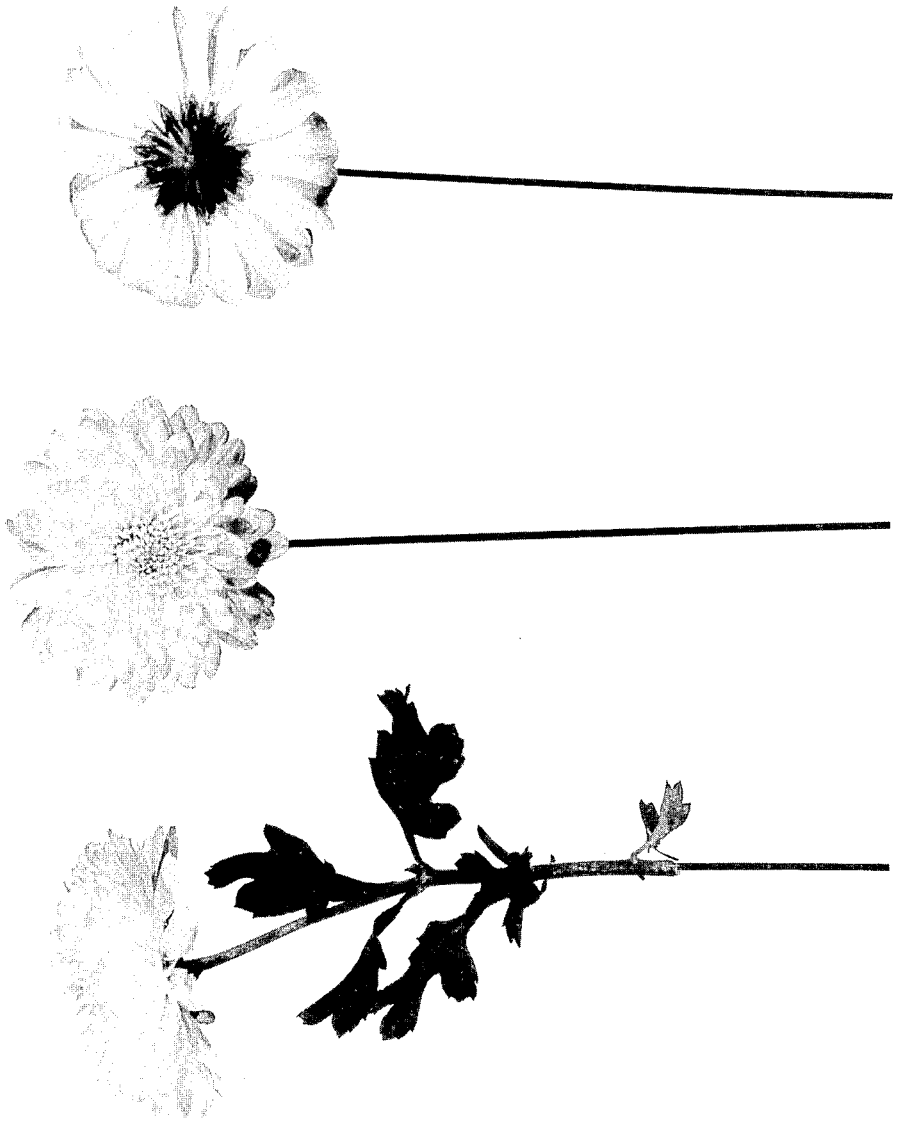

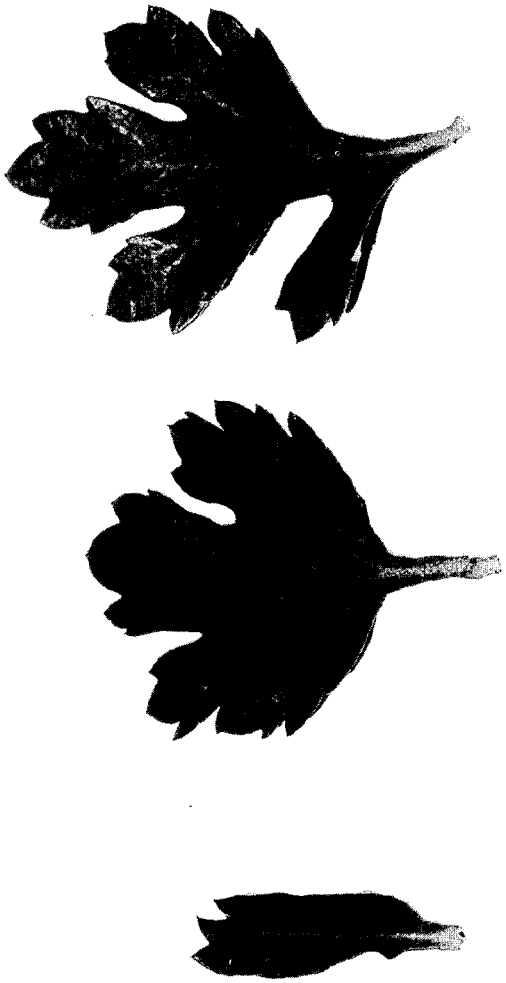

Plant Pat. 3,897
Patented June 1, 1976

3,897

CHRYSANTHEMUM PLANT

Grace H. Mack, New Canaan, Conn., and Walter H. Jessel, Jr., Doylestown, and William Erwin Duffett, Akron, Ohio, assignors to Grace H. Mack, New Canaan, Conn.

Filed Apr. 25, 1975, Ser. No. 571,476
Int. Cl. A01h *5/00*
U.S. Cl. Plt.—75 1 Claim

The present invention comprises a new and distinct cultivar of *Chrysanthemum morifolium,* Ramat., hereinafter referred to by the cultivar name Patriot (#71012-M01).

Patriot was originated from a cross made in a controlled breeding program by Grace H. Mack in New Canaan, Conn. in the year 1970.

The male or pollen parent, was Pixie Cushion (#664-15M03: U.S. Plant Pat. #3,454; commercially available) a decorative of yellow color originated by the present inventors from a cross between C84–62 (#21620E14; unnamed seedling) and MX514–63 (#21620E15; unnamed seedling).

The female or seed parent, was Snowbound (#21680-E09; unpatented; commercially available), a decorative of white color which is of unknown parentage.

Patriot was discovered and selected as a flowering seedling within the progeny of the stated cross by Grace H. Mack and Walter H. Jessel, Jr. on Oct. 5, 1971 in an outdoor field environment in Barberton, Ohio.

Patriot is a product of a planned breeding program which had the objective of creating durable white decoratives for outdoor natural season field culture that would fulfill in part or in whole the need for white decoratives with early response, compact and spreading growth habit, and prolific flowering traits.

The first act of asexual reproduction of Patriot was accomplished when vegetative cuttings were taken from the initial selection in February 1972 in a controlled environment in Barberton, Ohio by a technician under formulations established and supervised by William E. Duffett and Walter H. Jessel, Jr. Horticultural examination of selected units initiated Oct. 26, 1972, has demonstrated that the combination of characteristics as herein disclosed for Patriot are firmly fixed and are retained through successive generations of asexual reproduction.

Patriot has not been observed under all possible environments. The phenotype may vary significantly with variations in environment such as temperature, light intensity, and daylength. The following observations, measurements, and comparisons describe plants grown in a field in Barberton, Ohio under outdoor environmental conditions which are generally described in Local Climatological Data, Summary With Comparative Data, Akron, Ohio. U.S. Department of Commerce, National Oceanic and Atmospheric Administration, Environmental Data Service, Washington, D.C. 1972, 1973, 1975 and Tables of Sunrise, Sunset, and Twlight. Supplement to the American Emphemeris, 1946. U.S. Naval Observatory, Washington, D.C., p. 103.

The following traits have been repeatedly observed and are determined to be basic characteristics of Patriot which in combination distinguish this chrysanthemum as a new and distinct cultivar:

(1) Ivory white inflorescence color.

(2) Flat inflorescene form.
(3) Decorative inflorescence type.
(4) Diameter of face of inflorescence up to 2.25 inches at maturity.
(5) Short plant height.
(6) Compact, semi-upright plant growth habit.
(7) Average natural season flowering date of Sept. 20.
(8) Average controlled flowering response period of 6 weeks.

The accompanying photographic drawings show typical inflorescence and foliage characteristics of Patriot with colors being as nearly true as possible with illustrations of this type. Sheet 1 is a color photograph of Patriot. Sheet 2 is a black and white photograph showing three different views of the inflorescence of Patriot. Sheet 3 is a black and white photograph showing the foliage of Patriot at three stages of growth.

Of the many commercial cultivars known to the present inventors, the most similar cultivars in comparison to Patriot are Baby Tears (unpatented) and Pixie Cushion (U.S. Plant Pat. #3,454). Reference is made to Chart A attached at the end of the specification which compares ceratin characteristics of the above mentioned cultivars with the same characteristics of Patriot. General comparisons are as follows:

(1) In comparison to Baby Tears, Patriot has earlier natural season flowering date, larger diameter across face of inflorescence, less incurved inflorescence form, different inflorescence type, less spreading growth habit, and shorter controlled flowering response period. Plant height and inflorescence color of Patriot are similar to those of Baby Tears.

(2) In comparison to Pixie Cushion, Patriot has larger diameter across face of inflorescence, and ivory white inflorescence color. The natural season flower date, inflorescence form and type, plant height, growth habit and flowering response period of Patriot are similar to those of Pixie Cushion.

In the following description, color references are made to The Munsell Limit Color Cascade, 1972 edition. The color values were determined between 7:30 a.m. and 8:00 a.m. on Oct. 15, 1974 under 25 foot candle light intensity at Barberton, Ohio.

Botanical classification: *Chrysanthemum morifolium,* Ramat., cv Patriot.

I. INFLORESCENCE

A. Capitulum:
*Form.*—Flat.
*Type.*—Decorative.
*Color.*—Center of inflorescence: 26–3. Ray floret: Base of corolla: 26–3. Corolla (abaxial): White Corolla (adaxial): White.

B. Corolla of ray florets:
*Texture (adaxial).*—Glabrous.
*Appearance and form.*—Lugulate.
*Arrangement.*—Whorled on receptacle.
*Persistence.*—Resists shatter.

C. Reproductive organs:
*Androecium.*—Stamen: Syngenesious; 5 in number. Polen: Scant. Occurrence: Present disc florets only.
*Gynoecium.*—Ovary: Inferior; bicarpellate. Style: single. Stigma: 2-lobed.

II. PLANT

A. General apperance: Compact; short; semi-upright.
B. Duration and texture: Perennial; herbaceous.
C. Foliage:
*Color.*—Abaxial: 20–13 to 20–14. Adaxial: 20–11 overlaid with white.
*Shape.*—Spatulate; slightly lobed.
*Texture.*—Glabrous.
*Arrangement.*—Alternate.
*Veination.*—Prominent.
*Margin.*—Moderately serrated.

We claim:

1. A new and distinct cultivar of chrysanthemum plant characterized particularly as to uniqueness by the combined characteristics of ivory white inflorescence color, flat inflorescence form, decorative inflorescence type, diameter of face of inflorescence up to 2.25 inches at maturity, short plant height, compact, semiupright growth habit, average natural season flowering date of Sept. 20, and its average controlled flowering response period of 6 weeks.

CHART A—COMPARISION OF PATRIOT WITH BABY TEARS AND PIXIE CUSHION

| Cultivar | Natural season flower date | Diameter across face of inflorescence, inches | Inflorescence form and type | Plant height | Growth habit | Inflorescence color | Controlled flowering response period |
|---|---|---|---|---|---|---|---|
| Patriot | Sept. 20 | 2¼–2½ | Flat, decorative | Short | Compact, semi-upright | Ivory white | 6 weeks. |
| Baby Tears | Sept. 25 | 1¼–1½ | Semi-incurved pompon | do | Compact, semi-spreading | do | 7 weeks. |
| Pixie Cushion | Sept. 20 | 1½–1¾ | Flat, decorative | do | Compact, semi-upright | Yellow | 6 weeks. |

No references cited.

ROBERT E. BAGWILL, Primary Examiner